Figure 1:
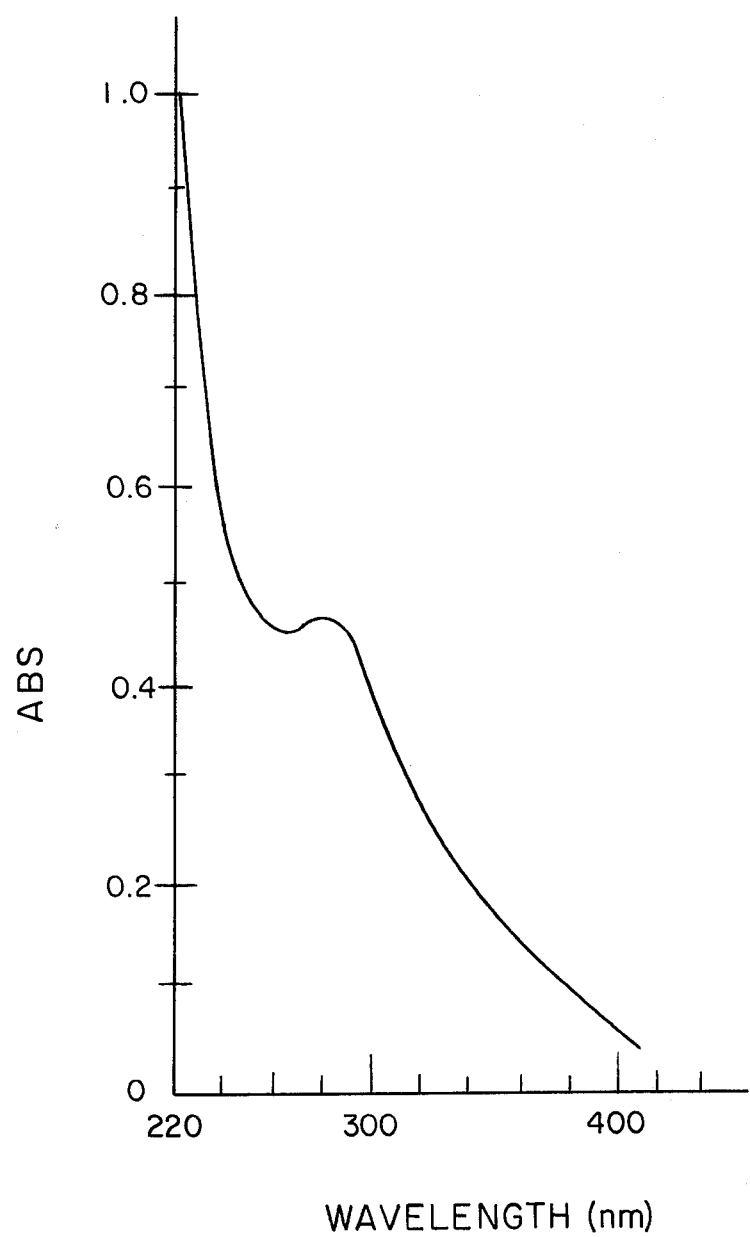

United States Patent [19]

Kojima et al.

[11] 4,440,761

[45] Apr. 3, 1984

[54] INTERFERON INDUCER, A PROCESS FOR PRODUCING THE SAME AND PHARMACEUTICAL COMPOSITION CONTAINING THE SAME

[75] Inventors: Yasuhiko Kojima, Yokohama; Seishi Konno; Takashi Hashimoto, both of Tokyo, all of Japan

[73] Assignee: The Kitasato Institute, Tokyo, Japan

[21] Appl. No.: 290,283

[22] Filed: Aug. 6, 1981

Related U.S. Application Data

[63] Continuation-in-part of Ser. No. 119,325, Feb. 7, 1980.

[30] Foreign Application Priority Data

Aug. 6, 1980 [JP] Japan ................................. 55-107955

[51] Int. Cl.$^3$ ............................................. A61K 35/78
[52] U.S. Cl. .................................................... 424/195
[58] Field of Search ........................................ 424/195

*Primary Examiner*—Stanley J. Friedman
*Attorney, Agent, or Firm*—Wolder, Gross & Yavner

[57] ABSTRACT

A process for producing an interferon inducer by extracting a substance having interferon inducing activity with water from the tissue of a plant selected from the genus Carthamus and variants thereof containing the said active substance to give an extracted solution, forming a supernatant from the extracted solution, fractionating the supernatant to yield fractions containing a major portion of the said active substance present in the supernatant and recovering the said active substance therefrom, characterized by fractionating the supernatant to yield fractions containing the said active substance having a molecular weight of from about 10,000 to about 200,000. Preferably the seed may be used as the tissue and the fractionation may be effected by ultrafiltration using a membrane capable of fractionating substances having the above-mentioned molecular weight.

10 Claims, 2 Drawing Figures

INTERFERON INDUCER, A PROCESS FOR PRODUCING THE SAME AND PHARMACEUTICAL COMPOSITION CONTAINING THE SAME

RELATED APPLICATION

This application is a continuation-in-part of Ser. No. 119,325 filed Feb. 7, 1980.

BACKGROUND OF INVENTION

This invention relates to interferon inducer, a process for producing the same and pharmaceutical composition containing the same. Interferon is a substance capable of acting upon animal or human cells to inhibit the growth of a virus and is a type of protein liberated from the cell in response to viral infection. The activity of interferon is specific with respect to an animal species and non-specific with respect to a viral species and may vary, with differing conditions for its induction. It is also known that the growth of certain animal tumour-type viruses may significantly be inhibited by interferon under certain conditions. A substance capable of acting upon animal or human cells to induce interferon is designated as an interferon inducer (hereinafter referred to as IF inducer). Thus an IF inducer is of potential interest in the prevention and treatment of various human and animal diseases caused by viral infection. However, various known IF inducers have never been used in practice for such a purpose because of certain serious defects. Thus is has been believed that IF inducers isolated from microorganisms are in general disadvantageous for therapeutic purpose because of their high toxicity.

Known mitogenic agents isolated from the tissues of higher plants such as phytohemagglitinin, pokeweed mitogen and concanavallin A have IF inducing activity. However, they have never been used for preventing and treating various diseases caused by viral infection with successful result because their IF inducing activity is extremely low. Other IF inducers isolated from the tissues of higher plants are also known. That is, Kojima et al disclosed an IF inducer isolated from the root of *Angellica acutiloba* Kitagawa (known in Japan as Toki) [Japanese Patent application as laid open to public inspection as Kokai Koho No. 32107/78] and Kojima and Tamamura disclosed an IF inducer isolated from the peeling of a mulbaeery such as *Morus alba* Linne or *Morus bombycis* Koidzmi [Japanese Patent application as laid open to public inspection as Kokai Koho No. 99313/78].

Subsequently, we provided an IF inducer having a high IF inducing activity and extremely low toxicity (hereinafter referred to as inducer A) originating from a plant of the genus Carthamus of the family Compositae or a variant thereof containing the inducer A, which may be prepared by extracting the tissue of such a plant with water at a temperature from ambient to the boiling point of the extraction mixture for a period sufficient to extract a major portion of the inducer A present in the tissue, forming a supernatant from the extracted solution to yield fractions containing a major portion of the inducer A present in the supernatant and recovering the inducer A therefrom. Preferred plants for the preparation of the inducer A are exemplified by *Carthamus tinctorius* Linne.; *C. lanatus* L.; *C. arborescens* L.; *C. baeticus* Nyman and variants thereof and the use of their flowers is preferred because the inducer A is particularly rich in the flowers. The recovery of the inducer A may preferably be effected by ultrafiltration using a suitable membrane for fractionating substances having a molecular weight of from about 200,000 to about 1,000,000 because the molecular weight of the inducer A is from about 100,000 to about 3,000,000 (mainly from about 200,000 to about 1,000,000). The elemental analysis of the inducer A is H: $6.54\pm0.3\%$, C: $41.9\pm0.3\%$, N: $2.39\pm0.3\%$ and P: $0.28\pm0.03\%$, which is believed to be a polymer of amino acids and sugars containing phosphoric acid [disclosed in our U.S. Pat. application Ser. No. 119,325 which is hereby cited as reference].

As a result of further studies, it has now been found that another IF inducer (hereinafter referred to as inducer B) is present in the tissues (in particular, achens) of the plants of the genus Carthamus or variants thereof and may be isolated therefrom in a similar manner to that applied to the isolation of the inducer A. The IF inducing activity of the inducer B is at least equal or superior to that of the inducer A and its toxicity is also extremely low.

SUMMARY OF THE INVENTION

Thus, an object of this invention is to provide an IF inducer.

Figure 2:
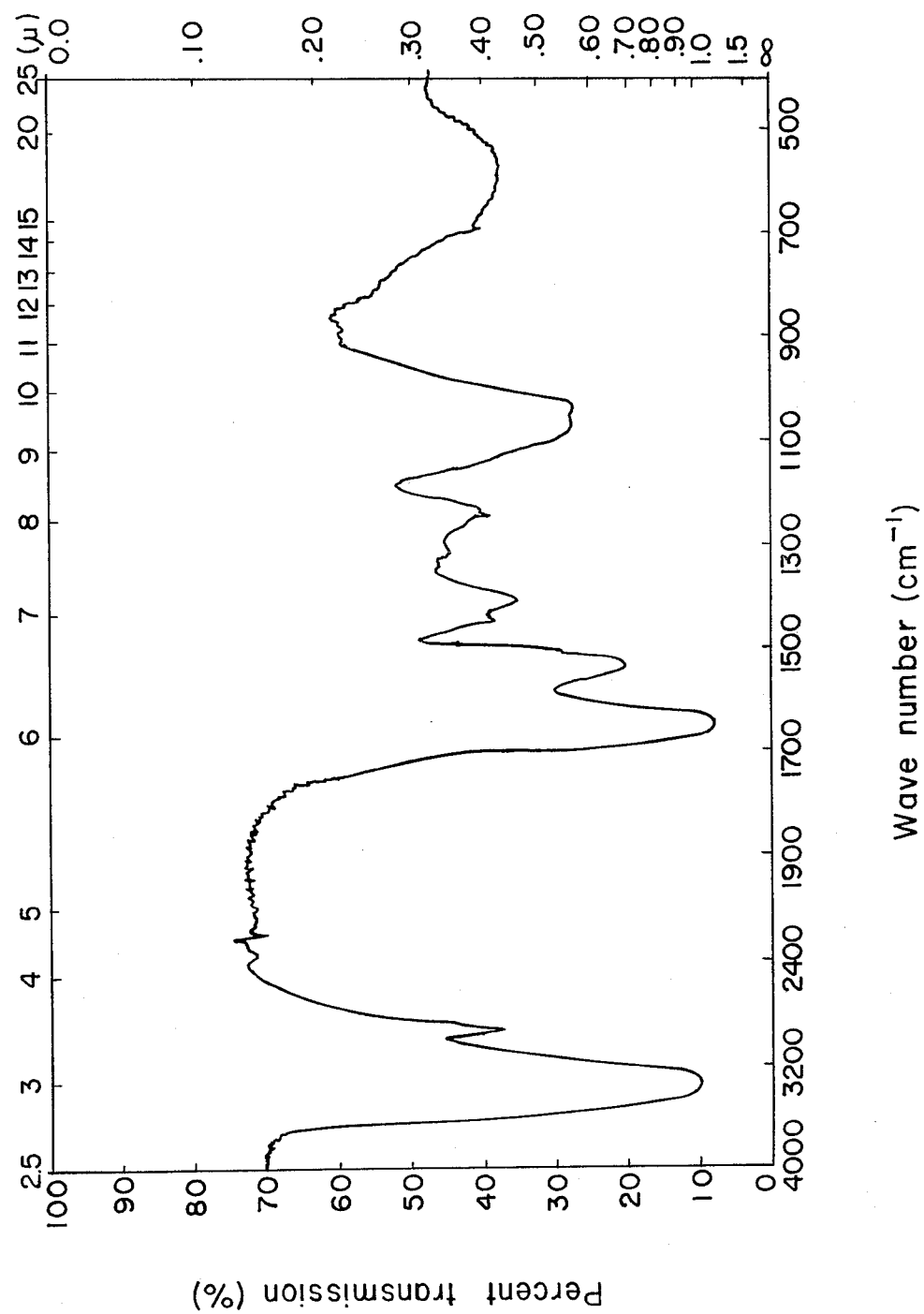

According to this invention, there is provided a substance having IF inducing activity which is stable in its substantially pure form of an amorphous whitish powder and which possesses the following physicochemical characteristics:

(1) Elemental analysis:
   Comprising carbon, nitrogen and oxygen.
(2) Molecular weight:
   About 10,000 to about 200,000, mainly about 20,000 to about 80,000.
(3) Melting or decomposing point:
   Melting point indefinite.
   Carbonized at about 190° C.
(4) Ultraviolet absorption spectrum:
   As shown in FIG. 1 (in 0.1 N NaOH solution) which is unchanged in water in IN NaOH solution.
(5) Infrared absorption spectrum:
   As shown in FIG. 2 (by KBr tablet method)
(6) Solubility in various solvents:
   Soluble in water, readily soluble in aqueous solutions of sodium hydroxide, potassium hydroxide and ammonium hydroxide.
(7) Color reaction:
   Positive in ninhydrin reaction, phenol/sulfuric acid reaction and Folin's reagent.
(8) Nature:
   Acidic

| (9) Main chemical constituents: | |
|---|---|
| Amino acids: | |
| Aspartic acid | |
| threonine | serine |
| glutamic acid | proline |
| valine | alanine |
| leucine | isoleucine |
| lysine | phenylalanine |
| thyrosine | histidine |
| amminia | |
| Sugars: | |
| Arabinose | galactose |
| glucose | mammnose |
| xylose | ribose |

(10) Heat stability:
Stable at 100° C. for 1 hour.

The molecular weight of the inducer B was determined by analytical ultracentrifugation using a Spinco Model E Analytical Centrifuge (commercial product of Beckmann Instrument Inc., U.S.A.), ultrafiltration using an Amicon Ultrafilter with XM50, XM100A and XM300 membranes (commercial products of Amicon Corpn., U.S.A.) and UK10, UK50 and UK200 membranes (commercial products of Toyo Roshi K.K., Tokyo) and gel filtration using Sephadex G-200 (commercial product of Pharmacia Fine Chemicals AB., Sweden). The ultracentrifugation was effected under the following conditions and one broad peak having gentle slopes on both sides was observed: A sample (0.5–1.0%) of the active substance was suspended in a neutral solution of 0.1 M sodum chloride and centrifuged at 20° C. at a maximum run of 60,000. Supplementarily column chromatography using gel filtration agents such as e.g. the series of Sepharose, Sephacryl (commercial products of Pharmacia Fine Chemicals AB., Sweden) and Bio-Gel (commercial products of Bio-Rad Laboratories Ltd., U.S.A.) were also used. All the results obtained were compared with the control values obtained, for example, by using standard references having identified molecular weights such as e.g. blue dextran 2000 ($*2 \times 10^6$), catalase from bovine lever ($*2 \times 10^5$), aldolase from rabbit muscle ($*1.58 \times 10^5$), albumin from bovine serum ($*6.7 \times 10^4$), ovalbumin from hen egg ($*4.3 \times 10^4$), chymotrypsinogen A from bovine punchrease ($*2.5 \times 10^4$) and ribonuclease A from bovine punchrease ($*1.37 \times 10^4$) [*standard molecular weight]. Throughout various fractions having different molecular weights, substantially the same elemental analysis and IF-inducing activity (determined by the method of hereinafter described Experiment 1) were found. From these results, in combination with a broad single band observed by the electrophoresis (cf. hereinafter described Experiment 2) and a high recovery ratio (cf. hereinafter described Experiment 4), it is found that the active substance of this invention is not a mixture but a high molecular weight polymer composed of polymers having substantially the same chemical and biological characteristics, of which major portion is present in a range of from about 20,000 to about 80,000 and the minor portion is present in a range of from about 10,000–20,000 and about 80,000–200,000.

The UV and IR absorption spectra were determined respectively by using Hitachi 340 Recording Spectrophotometer (commercial product of Hitachi Limited, Japan) and Shimazu Recording Infrared Spectrophotometer IR-27G (commercial product of Shimazu Seisaku-sho, Japan).

The amino acids present were determined by hydrolysis with 6 N HCl at 110° C. for 48 hours in varuo, followed by analysis using a Technicon Amino Acid Autoanalyzer Type NC-1 (commercial product of Technicon Corpn., U.S.A.) and the sugars present were determined by hydrolysis with 0.1 N sulfuric acid at 80° C. for 20 minutes and with 1 N sulfuric acid at 100° C. for 2 hours respectively, followed by analysis using a Technicon Sugar Autoanalyzer Type N-1 (commercial product of Technicon Corpn., U.S.A.).

The active substance of this invention is also preferably and readily soluble in alkaline solutions and substantially insoluble in organic solvents.

The following tests were effected to ascertain that the active substance of this invention represents an IF inducer.

(1) IF inducing activity:

Samples of the final product prepared by the method of hereinafter described Examples were used to induce IF in the cells and serum of the test animals and the activities of the resultant IF were determined by the method of hereinafter described Experiment 1. The results are shown in Tables 1 and 2, from which it is apparent that the IF inducing activity is positive.

TABLE 1

| Example No. | IF activity in vitro Concentration of sample ($\mu$g/ml) | | | |
|---|---|---|---|---|
| | 10 | 1.0 | 0.1 | 0.01 |
| 1 | >100 | >100 | >100 | 50 |
| 2 | >100 | >100 | >100 | 50 |
| 3 | >100 | >100 | >100 | 30 |
| 4 | >100 | >100 | >100 | 55 |
| 5 | >100 | >100 | >100 | 65 |
| 6 | >100 | >100 | >100 | 45 |
| 7 | >100 | >100 | >100 | 70 |

Dose = 500 $\mu$g/ml

The final product of hereinafter described Example 1 was administered to 5 rabbits by the method of hereinafter described Experiment 1 to obtain the results indicated in Table 2, from which it is apparent that the activities of the induced IF reaches their maximum 2 hours after administration. A similar tendency was also observed by using the samples prepared by other examples.

TABLE 2

| | Time of collection of blood after administration (hours) | | | | |
|---|---|---|---|---|---|
| | 0 | 1 | 2 | 4 | 6 |
| IF activity in vivo | >10 | 120 | 690 | 320 | 100 |

All seeds used in hereinafter described examples were located in Japan. For comparison purpose, the following seeds of *Carthamus tinctorius* were treated in a similar manner to that hereinafter described in Experiment 1, and no significant difference was found between these seeds: (1) Tuscon, Ariz., U.S.A. (2) Gila, University of Arizona, U.S.A. (3) Partial Hull, 14–5, Reduced Hull and Oleic Leed, University of California, U.S. Department of Agriculture (4) Paris, France, market grade (5) Culcutta, India, market grade.

From these results, it has been confirmed that the activity of the inducer B of this invention is at least equal to that of the inducer A as hereinbefore defined.

(2) Heat stability:

Samples (each 1 mg) of the inducer B were respectively dissolved in water (each 1 ml) and heated at 100° C. for 1, 4, 8 and 24 hours respectively. On each occasion, the sample was then treated by the method of hereinafter described Experiment 1 (in vitro method) to give the results shown in Table 3, from which it is apparent that the IF inducing activity of the active substance is more or less lowered after heating at 100° C. for 4 hours.

TABLE 3

| Heating time (hour) at 100° C. | Activity at concentration of sample ($\mu$g/ml) | | | |
|---|---|---|---|---|
| | 10 | 1.0 | 0.1 | 0.01 |
| Untreated | >100 | >100 | >100 | 60 |

TABLE 3-continued

| Heating time (hour) at 100° C. | Activity at concentration of sample (μg/ml) | | | |
|---|---|---|---|---|
| | 10 | 1.0 | 0.1 | 0.01 |
| 1 | >100 | >100 | >100 | 62 |
| 4 | >100 | >100 | 80 | <10 |
| 8 | >100 | 76 | <10 | <10 |
| 24 | 80 | <10 | <10 | <10 |

The IF inducers isolated from the flower and seed of Carthamus may be identified with each other as follows:

TABLE 4

| | (flower) | (seed) |
|---|---|---|
| Heat stability after heating at 100° C. | Stable by heating for 24 hours | More or less lowered by heating for 4 hours |
| IF activity by extraction with phenol/water | Inactivated | Increase |
| Amino acids (oxyproline) | + | − |
| Sugars (ribose) | − | + |
| Molecular weight | > about 200,000 | < about 200,000 |
| IR spectrum | | (different) |

The IF inducing activity of the inducer B is equal to or higher than that of the inducer A.

From the above-mentioned characteristics, it has been found that the active substance of this invention conforms to the widely recognized definition of any IF inducer because the inducer B as hereinbefore defined induced IF in animal cell or serum in vitro or in vivo, which is inactivated with 0.08% trypsin at 37° C. for 2 hours, and moreover its activity is specific with respect to an animal species and non-specific with respect to a viral species, as indicated in the undergoing experiment 1.

It is thus believed that the active substance of this invention is not only a new IF inducer but also a new substance because no such a substance has, to our knowledge, ever been reported in the art. For example, mitogenic agents such as phytohemagglutinin, pokeweed mitogen and cncanavallin A described in the literatures are types of protein having very weak IF-inducing activity whic his inactivated on heating at 56° C. for 5 hours, on the contrary to high heat stability and high IF-inducing activity of the active substance of this invention. The known IF inducers isolated from the root of *Angelica actiloba* Kitagawa is high molecular and its IF-inducing activity is not inactivated on heating at 100° C. for one hour. However, its chemical constituents and infrared absorption spectrum are different from those of the active substance of this invention. The known IF inducer isolated from the peeling of mulberry root contains as main constituent a 1-3 bonded glucose and has a different molecular weight. Moreover, the mitogenic activity which is found in the known IF inducers originating from bacterial endotoxin and higher plants such as *Angellica acutiloba* Kitagawa and mulberry is very low or not found in the IF inducer of this invention.

As to the plants of the genus Carthamus, for example, *C. tinctorius* Linne (safflower) and variants thereof have been cultured over many years for their yellow and red pigments contained in the flowers and their edible oil in the seed and moreover the flower of *C. tinctorius* has been used in Japan and China as Sino-Japanese traditional drug over many years. However, to our knowledge, the presence of a substance having interferon inducing activity in the tissue of this plant has never been reported in the art. Although it was previously known that *C. tinctcorius* contains, for example, carthamine, carthamone, neocarthamine and the like, all of such substances are low molecular weight substances having no IF inducing activity. [Cf. e.g. "Chinese Herbal Medicine, Ancient and Modern Science" by Richard Hyatt, page 123 (1978); "Chinese Herbs, Their Botany, Chemistry and Pharmacodynamics" by John D. Keys, pages 223-224 (1978); "Kanpo, Geschichte, Theorie und Praxis der Sino-Japanischen traditionellen Medizin" by Keisetsu Otsuka, page 175 (1976)].

The IF inducer of this invention i.e. the inducer B as hereinbefore defined may be produced basically by the same process for producing the inducer A as hereinbefore defined i.e. the process described and claimed in the parent application Ser. No. 119,325 which is hereby cited as reference. However, because the physicochemical characteristics of the inducer B from the inducer A as hereinbefore defined as well as of the seed from the flower, it is advantageous for practical purrpose to modify the process disclosed and claimed in the parent application. Thus, according to this invention, we provide a process for producing an interferon inducer by extracting a substance having IF inducing activity from the tissue of a plant of the genus Carthamus or a variant thereof containing the said active substance with water at a temperature from ambient to the boiling point of the extraction mixture for a period sufficient to extract a major portion of the said active substance present in the tissue, forming a supernatant from the extracted solution, fractionating the supernatant to yield fractions containing a major portion of the said active substance present in the supernatant and recovering the active substance therefrom, characterized by that the seed is extracted as the tissue.

Although the inducer B is mainly present in the seed of the plant, it is also possible to use any and all tissue for extraction and fractionating the supernatant by ultrafiltration using a membrane for fractionating substances having a molecular weight of from 10,000 to 200,000 (preferably from 20,000 to 80,000).

The process of this invention will be explained in the following specification.

Raw material:

Any and all seeds of the plants of the genus Carthamus or a variant containing the active substance B may be used as the starting material. Although some plants exemplified above in conjunction with the active substance A may also be used, the use of the seed of *Carthamus tinctorius* Linne (safflower) or a variant thereof containing the active substance B is most advantageous. This plant is useful, for example, as raw material for the production of rouge and edible oil and as feedstuff for cattle or poultry, foodstuff, medical herb and the like and thus has been cultured over many years in various countries of the world. On the contrary, one of the most serious defects inherent to various known IF inducers lies in their high toxicity. Moreover, although the seed of this plant is nowadays used for the production of edible oil on an industrial scale, the usage of the residue i.e. the seed cake (e.g. feedstuff for cattle on poultry) is, so to speak, relatively limited and thus it may be possible to supply a very large amount of the raw material for the process of this invention cheaply and easily.

As the raw material, it is possible to use the dried or fresh seed. However, the use of the dried seed is advantageous for better preservation and extraction efficiency. The seed consists of the hard hull and its contents, both containing the active substance of the present invention.

It is advantageous for better extraction efficiency to break the hull prior to extraction, and thus it is a good idea to use the seed cake, from which the edible oil has been extracted. For example, when a large amount of the edible oil contained in the seed of *Carthamus tictorius* (safflower) is extracted in conventional manner (e.g. by the hot press method, solvent extraction method and the like), the resultant residue i.e. seed cake may with advantage be used for the process of the present invention. For example, when the seed of *C. tinctorius* is treated in usual manner e.g. by using a screw press and extraction with hexane, the amount of the remaining oil in the seed cake is usually about 1%, and such a cake is used for example as feedstuff for cattle and poultry. However, with respect to the production yield and the activity of the active substance obtained by the process of this invention, no significant difference is observed between the extraction with water and the extraction with an organic solvent.

Extraction:

It is wise to effect the extraction with water, because it is safer, cheaper and easier in operation. Extraction with water may be effected at a convenient temperature e.g. from ambient to about 130° C. As the active substance B is soluble in water and readily soluble in aqueous alkaline solution (e.g. at a pH of 7–10), it is preferred to adjust the pH of the extracting water, for example, by using a suitable buffer solution, sodium hydroxide, potassium hydroxide, ammonium hydroxide and the like. The extraction may be effected over any convenient period of time, usually for 1–5 days at room temperature, which may be shortened if the extraction temperature is raised. Thus, for example, the extraction may be effected for 30 minutes to 6 hours at 40° to 120° C. By such a treatment, it is possible to extract the major portion of the active substance B contained in the seed (in some cases, more than 90%). If desired, it is also possible to add to the extracting water a suitable antiseptic agent. The extraction may be effected continuously or intermittently at a convenient ratio of water to the raw material (e.g. 5–10 folds by volume).

If desired, it is possible prior to the extraction to remove various impurities such as lipids contained in the seed by using a suitable organic solvent such as, for example, methanol, ethanol, chloroform, ether, hexane or a mixture thereof. Such a pre-treatment may be effected easily without the loss of the desired active substance. It is of course possible to extract the active substance from the hull and its cntents independently.

Alternatively, it is possible to extract the active substance of this invention from the seed by using a mixture of water and phenol. In this case, the concentration of the phenol in water is convenient (e.g. 20–60%, preferalby 35–50%) and the extraction may be effected at a convenient temperature for a suitable period of time (e.g. 10–60 minutes at 40°–80° C.).

Recovery:

The residue of the seed is removed from the extraction mixture in conventional manner, for example, by filtration, pressing, centrifugation and the like.

After this, undesired impurities such as pigments, low molecular substances and the like are removed from the resultant supernatant in order to allow recovery of the active substance of this invention. Preferred methods for this purpose are exemplified as follows.

(A) The supernatant is fractionated by ultrafiltration e.g. using a suitable membrane for retaining substances having a molecular weight of about 10,000 to about 200,000 (e.g. about 20,000 to about 80,000) because the active substance B is present in the fractions having a molecular weight of about 10,000 to about 200,000 (mainly about 20,000 to about 80,000). Thus, for example, the ultrafiltration may be effected at a pressure of 0.1 to 5 kg/cm$^2$. The active fractions are collected and combined, and the combined fractions are freeze-dried to obtain a whitish powder.

When the extraction is effected by using a mixture of water and phenol, it is necessary prior to extraction to remove completely phenol and other solvents which may injure the ultrafiltration membrane.

(B) The supernatant is, if desired, concentrated under reduced pressure and is then added with a hydrophilic organic solvent such as, for example, methanol, ethanol, propanol, butanol, acetone and the like at a convenient concentration (e.g. 40–70% v/v) so as to form a precipitate containing the active substance B, which is then, if desired, desalted by dialysis using a cellulose tube or concentrated under reduced pressure. After this, the solution is freeze-dried to obtain a whitish powder.

(C) instead of the organic solvent, it is possible to add to the supernatant an ammonium salt (e.g. ammonium chloride, ammonium sulfate, cetylmetylammoniumbromide and the like) or an inorganic metalic salt (e.g. zinc chloride, copper chloride and the like) at a convenient concentration (e.g. 20–50% v/v) so as to give a precipitate containing the active substance B. The precipitate is desalted, for example, by dialysis using a cellulose tube or by ultrafiltration using a suitable membrane for fractionating substances having a molecular weight of 5,000 or 10,000. After this, a whitish powder is obtained by freeze-drying the residual substance.

In this manner, it is possible to recover the major portion of the active substance B contained in the starting material (in some cases, more than 90%). However, the quantity of impurities contained in the crude powder is lowest in the case of (A) and also method (A) may be effected simpler and cheaper in operation. Moreover, it has been confirmed that even when a large amount of the crude powder obtained by method (A) is orally administered to animals without any further purification, no serious side effect may be avoided and thus such a crude powder may be used in practice for oral administration.

Purification:

Because the active substance B obtained by the process of this invention is a water-soluble acidic substance, it is thus possible to purify the crude product further in conventional manner used for the purification of various substances of this type, for example, by column chromatography using a suitable agent for gel filtration or ion exchanger. In the former case, the elution may be effected with water, although it is possible to use a suitable buffer solution for elution. In the latter case, the elution may be effected with a suitable buffer solution.

Preferred agents for gel filtration include, for example, Sephadex G-50 to G-200, Sepharose 2B to 6B and Sephacryl S-200 or S-300 (commercial products of Pharmacia Fine Chemicals AB., Sweden). Bio Gel P-30 to P-300 or Bio Gel A (commercial products of Bio-Rad Laboratories Ltd., U.S.A.), Sagavac (commercial product of Saravac Laboratories Ltd., UK.) and the like, and preferred agents for gel filtration are exemplified by DEAE Sephadex A-25 and A-50 (Cl+ form), QAE Sephadex A-25 and A-50 (Cl+ form), CM Sephadex C-25 and C-50 (Na+ form), DEAE Sephacel (Cl+ form), DEAE Cepharose Cl-6B (Cl+ form), CM Sepharose Cl-6B (Na+ form) (commercial products of Pharmacia Fine Chemicals AB., Sweden) and the like. It is also possible to use a suitable anion or cation exchange cellulose for purification. The product thus-obtained may contain certain impurities, although its IF inducing activity is sufficient for practical uses. If desired, the amount of impurities may further be reduced by cobiming these treatments.

According to a further aspect of this invention, there is provided a process for inducing an IF in the body or cells of human or animal, which comprises administering an effective amount of the inducer B as hereinbefore defined to a human or IF-inducing animal.

The active substance of this invention may be used solely or in combination with the inducer A as hereinbefore defined in a similar manner to that applied to the use of the inducer A. Thus, the active substance of this invention may be used without any toxicic trouble which is inherent to various known IF inducers such as e.g. poly I:C, endotoxin and the like.

Accordingly, it is possible to use the inducer B of this invention not only for preventing and curing various virally caused diseases of various vetebrates such as, for example, humans, mammals (e.g. cattle, horse, pig etc.), birds (e.g. fowl, duck etc.), fishes (e.g. rainbow trout etc.) and the like but also as anti-tumor agent, agent for improving overall healthy conditions for humans and animals.

The active substance of this invention may be administered e.g. by intravenous or intraperitoneal administration, intestinal or oral administration, spraying and the like.

In the case of intravenous admininstration, it may be possible to administer the active substance at a dose of 0.001 to 100 mg/kg/day, calculated as the final product. However, such a dose may vary, depending upon, for example, the type, age and weight of the host and various other conditions, among which the response of the host to IF induction and the purpose of the administration are most important. The active substance of this invention may preferably be administered to animals, for example, at a daily dose of 0.01 to 10 mg/kg (iv.) or 0.1 to 10 mg/kg (ip.) and to humans at a daily dose of 0.01 to 1.0 mg/kg (iv.) by injection. In the case of oral administration, it is possible to use, for example, more than about 10 times of the dose for intravenous administration. When the administration is effected topically or in a shorter period of time, a larger amount of the active substance may be used. When the dose is excessively small, it may be difficult to induce IF in the body or cells of the host. However, the use of an excessively large amount of the active substance of this invention may, in general, give rise to no serious side effect because its toxicity is extremely low.

It has also been found that when a suitable amount of any IF is administered to a host, followed by administering the active substance of this invention, the activity of the IF induced by the active substance of this invention may significantly be enhanced and for example about 3–10 folds activity may be obtained thereby. Moreover, it is possible in this manner to enhance considerably the response to the host to IF induction and also to extend the effective period of time of the IF induced.

The following samples were used in the following tests:

Sample B . . . The finally purified product by the method of Example 1.

Sample C . . . The finally purified product by the method of Example 2.

As test animals, rabbits (same type as that used in hereinafter described Experiment 1), mice (weight 25±1 g, ddy-strain 6 weeks old) and fowls (weight about 230 g, White Leghorn, 30 days old, female) were used.

(A) IF INDUCTIoN AND DETERMINATION OF IF ACTIVITY (I) In Invitro method:

A spleen cell suspension ($10^7$ cells/ml) was prepared by the method of hereinafter described Experiment 1 using an Eagle MEM medium (commercial product of Nissui Seiyaku K.K., Tokyo) containing a 10% calf serum (which was replaced by a 10% fetal cattle serum in the cases of human tests), each of which fraction (1 ml) was added with a given concentration of the sample and incubated overnight at a given temperature. The cultured liquor was centrifuged to separate a supernatant which was used for determining the IF activity induced. In the case of humans, the fresh spleen was collected from a man (adult deceased by external wounds) and used for the preparation of a leucocytes suspension on each occasion, and also blood was collected from the vein at the upper arm of a man (adult), from which the serum was separated to use for the preparation of a serum suspension of each occasion.

The IF activities were determined by using the cells shown in Table 5 in a similar manner to that hereinafter described in Experiment 1.

TABLE 5

| | IF induction in vitro | | |
|---|---|---|---|
| | I | II | III |
| Rabbit | 3 | 25 | RK-13 |
| Mouse | 30 | 37 | L |
| Human spleen | 2 | 25 | FL |
| Human leucocytes | 5 | 37 | FL |
| Fowl (White Leghorn) | 5 | 37 | Fibroblast |

I: Numbers in each group
II: Cultured for 24 hours at a temperature of (°C.)
III: Cells used for determination The results are shown in Table 6.

TABLE 6

| | | IF activity in vitro | | | | | |
|---|---|---|---|---|---|---|---|
| | | Concentration (μg/ml) | | | | | |
| | Sample | 100 | 10 | 1.0 | 0.1 | 0.01 | 1.0* |
| Rabbit | B | 460 | 480 | 470 | 230 | 100 | 160 |
| | C | 500 | 470 | 210 | 90 | 90 | |
| Mouse | B | 420 | 210 | 150 | 80 | 20 | 75 |
| | C | 490 | 320 | 144 | 76 | 22 | |
| Human | | | | | | | |
| (spleen) | B | 35 | 43 | 45 | 20 | <10 | <10 |
| (leucocytes) | B | 28 | 20 | 15 | <10 | | |
| Fowl | B | 63 | 35 | 20 | <10 | | |

*Control = Poly I:C (II) In vivo method:

(1) Rabbit:

Table 2 shows the IF activities induced in rabbits by the method hereinafter described in Experiment 1.

TABLE 2

| | IF activity (in vitro) | | | | |
|---|---|---|---|---|---|
| | Time of collection of blood after administration of sample | | | | |
| | 0 | 1 | 2 | 4 | 6 (hours) |
| Rabbit | <10 | 120 | 690 | 320 | 100 |

*Dose: 500 µg/ml

Similar treatments were repeated by changing the dose of the sample stepwise within a range of 4 to 0.004 mg/kg, and it was found that the IF activity induced in the serum reached its maximum 2 hours after administration. Also, the maximum was observed about 10 to 13 hours after oral administration.

(2) Mouse:

Mice (each group consisting of 10 mice) were used as test animals and treated as follows.

(a) Each 0.1 ml of a physiological solution of sodium chloride containing a given amount of sample B shown in Table 4 was injected into the vein at the tail of each mouse which was then allowed to stand for 1, 2, 3 or 5 hours, or (b) Each 0.2 ml of a physiological solution of sodium chloride containing a given amount of sample B shown in Table 7 was administered (ip) to each of the mice which was then allowed to stand for 2, 4 or 6 hours, or (c) Water (0.2 ml) containing a given amount of sample B shown in Table 7 was orally administered to each mouse which was then allowed to stand for 2.5, 5, 7.5, 10 or 13 hours, one each occasion.

On each occasion, the test animal was then sacrificed by cardic puncture. Blood was collected from each mouse and used to prepare the serum. The IF activity induced was determined in a similar manner to that described above. It was observed that the IF activity reached its maximum about 2 hours in the case (a), about 3–4 hours in the case (b) and about 7.5–10 hours in the case (c), after administration. Table 7 indicates the maximum IF activities (mean value). A similar tendency was also found when the same treatments were repeated by using sample A instead of sample B.

TABLE 7

| Maximum IF activity in vivo (mouse) | | | |
|---|---|---|---|
| Concentration (mg/kg) | Intravenous | Ip. | Oral |
| 4000 | | | 45 |
| 400 | | | 25 |
| 40 | 2364 | 500 | 14 |
| 4 | 1180 | 110 | <10 |
| 0.4 | 160 | 40 | |
| 0.04 | 80 | <10 | |
| 0.004 | 30 | <10 | |
| Untreated | <10 | <10 | <10 |

(3) Humans:

Each 200 mg of sample B was orally administered to each of five men (adults, healthy). Blood was collected from the vein at the arm of each volunteer after 13 hours from administration and used for the preparation of the serum which was then treated in a similar manner to that described above to determine the IF activity of about 14 units (mean value).

(4) Fowl:

Fowls (each group consisting of 10 chickens) were used as test animals. A physiological solution of sodium chloride (each 0.2 ml) containing sample B (4 mg/kg) was administered into the vein under the wing of each animal. After 2 hours on each occasion, the fowl was sacrificed by cardic puncture. Similarly, blood was collected for use to determine that the IF activity induced in the serum was about 26 units.

(B) PROTECTION AGAINST VIRAL INFECTIONS (1) Mouse (Vaccinia virus):

Mice (each group consisting of 20 female) were used as test animals, to each of which was administered a physiological solution of sodium chloride (each 0.2 ml) containing a given amount of the sample shown in Table 5 intravenously, intraperitoneally or orally. After 24 hours, each mouse was infected with Vaccinia virus at a dose of 30 $PFD_{50}$ [1 $PFD_{50}$ denotes an amount of the virus capable of forming the pocks at the tails of 50% of the mice used] contained in 0.1 ml of a physiological sodium chloride solution by injecting into the vein at the tail. For 9 days after this, the numbers of the pocks formed at the tail were compared with the corresponding numbers of the pocks found in the untreated mice (27.0 in average) to determine the inhibition ratio. A ratio of more than 50% was evaluated as an effective ratio. The results are shown in Table 8. In this table, the numbers of the pocks found in the untreated group wwere 28 in average.

TABLE 8

| | Inhibition ratio in average (%) | |
|---|---|---|
| Concentration | (mg/kg) | Sample B |
| Iv. | 40 | 72 |
| | 4 | 96 |
| | 0.4 | 82 |
| | 0.04 | 62 |
| Ip. | 40 | 65 |
| | 4 | 73 |
| | 0.4 | 72 |
| | 0.04 | 50 |
| Oral | 4000 | 57 |
| | 400 | 20 |

(2) Mouse (Herpes Simplex virus):

Herpes Simplex virus was used instead of Vaccinia virus. In a similar manner to that described in B(1), the samples were injected (iv. or ip.) or orally administered with the sample and the virus was infected by injection (ip.). After this, the test animals were observed for 30 days to investigate the survival days which were then compared with the corresponding days of the untreated group. A significant effect on the elongation of the life spun was observed.

(3) Rabbit (Vaccinia virus):

(a) Rabbits (each group consisting of 5 rabbits) were used as test animals, and a physiological sodium chloride solution (each 0.1 ml) containing sample A was injected into the skin at the back of each animal. After 24 hours, a physiological solution of sodium chloride (each 0.1 ml) containing 10 $ID_{50}$ of the virus [1 $ID_{50}$ denotes an amount of the virus used when 50% of the pocks formed under the skin of the test animal are more than 6×6 mm in size] was injected into the same place, and the numbers of the formed pocks were counted on the 7th day from the infection. The sample of the active substance used was stepwise diluted (×10) within a range of from 0.02 to 200 µg. It was found that a dose of more than 2 µg resulted in a 100% inhibition ratio.

(b) Each rabbit of the test group (each group consisting of 5 rabbits) was orally administered with sample A (each 100 mg/day) 5 times (on the first, 3rd, 4th, 6th and 8th days). On the 5th day, 10 $ID_{50}$ and 100 $ID_{50}$ of the virus were separately injected into the skin at the back of each rabbit. On the 12th day, it was observed that no pock was formed on the rabbits infected with 10 $ID_{50}$ and a minute quantity of the pocks was formed on the rabbits infected with 100 $ID_{50}$. However, the latter pocks disappeared completely in about 2 weeks.

(C) ANTI TUMOUR EFFECT (MOUSE)

(1) Ehrlich ascites tumour:

Mice (each group consisting of 15 mice) were used as test animals. A sterlized water (each 0.2 ml) containing Ehrlich ascites tumour cells ($2.5 \times 10^6$ cells/0.2 ml) was transplanted into each mouse by injection (ip.). 24 hours after this, a given amount of sample B in sterilized water (each 0.2 ml) was given to each animal. The administration was effected once daily for 17 days at a daily dose of 0.2, 1.0 or 5 mg/kg (ip) or 40, 200 or 1000 mg/kg (orally). By administration of 1 or 5 mg/kg/day (ip), the median survival days were more than 60 days and moreover, 2/3 of the test mice were still alive 80 days after transplantation and completely be cured. All mice of the untreated group were not alive on or after 30 days from the transplantation.

A similar effect was found when the sample was injected (ip) 5 times (1.0 mg/kg/day) at an interval of 3 days. Also, a similar effect was found by oral administratation of 100 mg/kg/day.

(2) S-180 Sarcoma Solid tumour:

Mice (each group consisting of 15 mice) were used as test animals. A sterilized water (each 0.2 ml; containing $1 \times 10^5$ tumour cells) was transplanted into each mouse under the skin at the armpit. Sample B was given to the mice in a similar manner to that described above. At a daily dose of 5 mg/kg (ip.)/mouse, the median survival days were more than 60 days and on or before 60 days after the transplantation, the tumours of 4 mice were reduced to about ⅓ in size and 4 mice completely cured. By administration of 400 or 1000 mg/kg/day orally, the results obtained were similar to the results obtained by injection (ip.). All mice of the control group deceased on or before the 33th day after transplantation.

(C) COMBINED USE OF IF AND IF INDUCER (PRIMING EFFECT)

(1) A suspension containing lymphoid cells of rabbits ($10^7$ cells/ml) was prepared by the method of hereinafter described Experiment 1 and was added with rabbit IF (30 unit/ml). The mixture was treated at 37° C. for 6 hours and was then centrifuged to remove the IF. Then an Eagle MEM medium (1 ml) and sample B were added to the cells and its activity was determined with simultaneous change of the amount of sample B from $10^{-3}$ to $10^{-7}$ mg/ml. It was found that the activity of the induced IF raised to about 3-10 folds and also the response to the cells was significantly improved.

(2) By the method of hereinbefore described (D,1), a suspension of human spleen cells ($10^7$ cells/ml) was prepared and treated with human IF (100 unit/ml). The activity of the IF raised to about 3-6 folds and also the response of the cells to the IF was improved significantly.

(3) Each of rabbits (each group consisting of 5 rabbits) was intravenously administered with rabbit IF (each $10^6$ units) and after 6 hours sample B was administered in a similar manner to that described in (A) (II) (1). It has been found that the IF activity in the serum was raised to about 3 to 10 folds and also the effective period of time of the IF induction was extended.

(4) Each of rabbits (each group consisting of 5 rabbits) was intravenously administered with rabbit IF (each $10^6$ units). On the next day, a test on the protection of viral infection was begun in a similar manner to that described in (B) (3) (b). No pock was formed at the sites infected with 10 $ID_{50}$ of the virus. Minor pocks were formed at ⅓ of the locations infected with 100 $ID_{50}$ of the virus, which were however disappeared completely in 2 weeks after the infection.

(E) Toxicity (1) Acute toxicity:

A physiological sodium chloride solution containing sample B was administered to each of the mice (male and female; each group consisting of 20 mice) and rats (male and female; weight about 95 g; SPF-SD strain; 6 weeks old; each group consisting of 20 rats) to obtain the $LD_{50}$ values shown in the following table, from which no significant difference was observed between male and female.

TABLE 10

| | Acute toxicity ($LD_{50}$) | | | |
| | Concentration of sample (g/kg) | | | |
| Animal | Subcutaneous | Ip | Iv | Oral |
|---|---|---|---|---|
| Mouse | >2 | >1.5 | 1.3 | >5 |
| Rat | >2 | >1.5 | 1.1 | >5 |

(2) Subacute toxicity:

Rats (weight about 95 g; SPF-SD strain; 6 weeks old; each group consisting of 20 rats) were used as test animals. Sample A was divided into fractions (0.35, 0.7, 1.4 and 2.8 g/kg), each of which was added to each sterilized water (from 0.25 to 0.5 ml), and a given amount of the sample was daily administered to the test animals compulsively by using a canule. The administration was continued for 3 months. In comparison with the untreated animals, the healthy conditions of the test animals were improved throughout the test period and their body weights increased at a remarkably high ratio. All animals were dissected after the end of 3 months and investigated pathologically. However, it was difficult to determine the subacute toxicity reasonably because no significant change was observed pathlogically.

(b) Five healthy men (adults) were administered orally with sample A (200 mg/day) and the administration was continued for 10 days. As a result, no significant side effect was observed.

For the purpose of administering the active substance of this invention to humans and animals with good results, there is provided a pharmaceutical composition, which comprises as active ingredient an effective amount of the active substance of this invention as hereinbefore defined, in association with a pharmaceutical carrier or excipient.

The composition may be any and all forms adapted to oral, rectal, perenteral, percutaneous, intramucous administration and the like. Thus, for example, the composition may be solid or liquid for oral administration and may take the forms of powders, syrups, capsules, granules, emulsions, suspensions, drops and the like. Such composition comprises carrier or excipient conventionally used in the pharmaceutical art. Thus, for example, suitable tabletting excipients include lactose, potato and soluble starch and magnesium stearate, and for parenteral administration, the carrier may be a steril water, physiological solution of sodium chloride, armond oil and the like, which may be put in an ampule or may be added to the active substance before use.

The composition may, if desired, further comprises, for example, bonding agents, stabilizing agents, emulsifiers, suspending agents, dispersing agents, lublicants, antiseptic agents, fillers and the like conventionally used in the pharmaceutical art. Such composition comprises carrier or excipient conventionally used in the pharmaceutical art. Thus, for example, suitable tabletting excipients include lactose, potato and soluble starches and magnesium stearate and for parenteral administration, the carrier may be a sterile water, physiological solution of sodium chloride, armond oil and the like, which may be put in an ampule or may be added to the active substance before use.

The composition may, if desired, further comprise, for example, bonding agents, stabilizing agents, emulsifiers, suspending agents, dispersing agents, lublicants, antiseptic agents, fillers and the like conventionally used in the pharmaceutical art.

For practical purpose, the composition may be formulated, for example, as buccals, troches, eye drops, suppositories and the like for intramucous administration, solutions, oils, suspensions and the like for injection agents, inhalants, sprays and the like for inhalational administration and ointments, plasters, liniments, bathes, sprays and the like for external administration.

Advantageously, the composition may be formulated as dosage units, each unit being adapted to supply a fixed dose of active ingredient. Suitable dosage unit forms are, for example, tablets, coated tablets, ampules, capsules, suppositories and the like.

The amount of the active ingredient preferably contained in such dosage unit forms may, for example, be within a range of from about 4 to about 10 for oral administration, about 2–3 for subcutaneous administration, about 1.5–3 for intramuscular administration, about 2–4 for baccals and troches and about 5–10 for suppositories, calculated on the basis of the preferred amount for intravenous injection. Examples of unit dosage forms are as follows.

| (1) Parenteral injection: | |
|---|---|
| Physiological solution of NaCl | 1.0 ml |
| Sample B | 0.01 g |
| packed and sealed in a 2 ml ampule under sterilized conditions. | |
| (2) Troch: | |
| White sugar | 1 g |
| Sample B | 0.05 g |
| Starch | 0.05 g |
| (3) Suppository: | |
| Polyethylene glycol 400 | 0.8 g |
| Liquid polyethylene glycol 1500 | 0.2 g |
| Sample A | 0.2 g |
| (4) Syrup: | |
| CMC-Na | 0.2 g |
| Simple syrup | 20 g |
| Ethylparaffin | 0.04 g |
| Sample B | 0.1 g |
| (5) Ointment: | |
| Purified lanolin | 5 g |
| Yellow wax | 5 g |
| White vaselin | 87 g |
| Sample B | 3 g |
| (6) Liniment: | |
| Potassium hydroxide | 0.3 g |
| Glycerin | 20 ml |
| Ethanol | 25 ml |
| Sample B | 2.5 g |
| Make-up water | to 100 ml |

DRAWINGS:

FIGS. 1 and 2 show respectively the ultraviolet and infrared absorption spectra of the active substance of this invention.

The following non-limiting examples illustrate the invention.

EXAMPLE 1

Dried seeds (100 g) of *Carthamus tinctorius* Linne were crushed and extracted by allowing to stand in water (1000 ml) at room temperature for 3 days. The solution was centrifuged (10,000 r.p.m.) for 20 minutes to separate the supernatant from the residue. The residue was washed twice with water (each 500 ml) and the washing liquid was combined with the supernatant. The combined solution were treated by ultrafiltration using an ultrafilter (MC-4A, commercial product of Bio Engineering K.K., Tokyo) with XM-100A membrane (commercial product of Amicon Corpn., U.S.A.) for fractionating substances having a molecular weight of 100,000 at a pressure of 3 kg/cm$^2$. The solution thus-obtained was further treated by ultrafiltration using XM 10 membrane (commercial product of Amicon Corpn., U.S.A.) for fractionating substances having a molecular weight of 10,000. The residue was collected and freeze-dried to obtain a whitish powder (212 mg). This powder was dissolved in water (5 ml) and transferred to a column (4.5×70 cm) packed with Sephadex G-100 (commercial product of Pharmacia Fine Chemicals AB., Sweden) and eluted with water (1200 ml). The effluent was divided into fractions (each 5 ml) and Fraction Nos. 60–150 were collected and combined, and the combined fractions were desalted and freeze-dried to give a whitish powder (55.2 mg). For further purification, this powder was dissolved in a 0.01 M tris-HCl buffer solution (5 ml; pH 7.0; I=0.01) and tranferred to a column (2.5×70 cm) packed with DEAE-Sephadex A-50 (commercial product of Pharmacia Fine Chemicals AB., Sweden). The elution was effected with a 0.2 M tris-HCl buffer solution (500 ml; pH 8.6; containing 0.5 M sodium chloride) and the effluent was divided into fractions (each 5 ml). Fractions Nos. 20–40 were collected and combined, and the combined fractions were desalted by ultrafiltration using a PM-10 membrane (commercial product of Amicon Corpn., U.S.A.) capable of fractionating substances having a molecular weight of 10,000, followed by freeze-drying to obtain an amorphous whitish powder (33.1 mg), of which IF activity was higher than that of the first whitish powder.

EXAMPLE 2

Dried seeds (100 g) of *C. tinctorius* Linne were crushed and added with water (1000 ml). After extraction at 100° C. for 60 minutes, the extracted solution was treated in a similar manner to that described in Example 1 to obtain a whitish powder (41.2 mg).

EXAMPLE 3

Dried seeds (100 g) of *C. tinctorius* Linne were crushed and added with water (1000 ml). The extraction was effected at 120° C. for 60 minutes in an autoclave (1 atu.), followed by a similar treatment to that described in Example 1 to result in a whitish powder (43.4 mg).

EXAMPLE 4

Dried seeds (100 g) of *C. tinctorius* Linne were crushed and allowed to stand at 4° C. overnight in acetone (500 ml). The extracted solution was filtered by using a filter paper to give a residue which was then added with acetone (500 ml) and the extraction was effected at room temperature for 60 minutes with shaking to give a residue. In this manner, the extraction with acetone was repeated five times in total and the residue thus-obtained was dried in vacuo to remove acetone. The dried substance was added with water (100 ml), extracted at 100° C. for 60 minutes and treated in a similar manner to that described in Example 1 to yield a whitish powder (44.6 mg).

EXAMPLE 5

A similar treatment to that described in Example 4 was carried out by using a mixture of chloroform and methanol (500 ml; 1:1 v/v) to obtain a whitish powder (30 mg).

EXAMPLE 6

Dried seeds (100 g) of *C. tinctorius* Linne were squeezed by using a press and water (1000 ml) was added to the residue. The extraction was effected at 100° C. for 60 minutes and the extracted solution was treated in a similar manner to that described in Example 1 to obtain a whitish powder (37.6 mg).

EXAMPLE 7

Dried seeds of *C. lanatus* Linne (100 g) were crushed and added with water (500 ml). The mixture was heated to 68° C. and was added with a phenol solution (500 ml; 90%; 68° C.). The extraction was effected for 20 minutes with agitation. The extracted mixture was cooled to room temperature and centrifuged (7000 r.p.m.) for 20 minutes to separate the water layer (upper layer), phenol layer (middle and lower layers) and residue from each others. After the recovery of the water layer, the remaining phenol layer and residue were added with water (400 ml) and extracted at 68° C. for 20 minutes. The thus-obtained water layer was recovered and combined with the first water layer, and the combined water layers were put into a cellulose tube for dialysis which was effected against deionized water at 4° C. for 3 days. The thus-obtained solution was treated in a similar manner to that described in Example 1 to obtain a whitish powder (25.0 g).

EXPERIMENT 1

Determination of IF induced by IF inducer and IF assay: [Reference: Y. Kojima's report in Kitasato Arch. Med., 43:35 (1970)]

(a) IF induction in vitro:

A rabbit (weight about 1 kg; New Zealand White; SPF) was sacrificed by cardic puncture and its spleen, bone marrow and lymph node cells were collected and combined together, from which a cell suspension containing the mixed cells ($10^7$ cell/ml) was prepared using an Eagle MEM medium (commercial product of Nissui Seiyaku K.K., Tokyo) containing a 10% calf serum. This suspension was divided into fractions (each 1 ml), and 4 fractions were respectively added with 10, 1.0, 0.1 and 0.01 μg/ml of an active substance prepared by the method of Example 1, which was incubated at 25° C. for 24 hours, followed by centrifugation to obtain each supernatent which was then used to determine the activity of the IF induced.

(b) IF induction in vivo:

An aqueous solution (2 ml) of the active substance prepared by the method of Example 1 (500 μg/ml) was injected into the auticular vein of a rabbit (weight about 1 kg; New Zealand White; SPF). 1, 2 4 and 6 hours after this, a 2 ml sample of blood was removed from the rabbit on each occasion and used to prepare the serum used to determine the IF activity.

(c) Determination of IF activity:

In both (a) and (b), the activity of the IF induced was determined in reliance with the reduction ratio of plaques in the following manner.

A monolayer culture of the lined cells RK-13 of rabbit was put in a dish and added with a predetermined amount of the solution obtained by the method (a) or (b) (suitably diluted). The culture was incubated at 37° C. overnight. Then the cultured was added with Vesicular atomatitis viruse used as the challenge virus and inculbated at 37° C. overnight. The IF activity is indicated by the reduction ratio of plaques and the unit of the IF activity is expressed by the reciprocal number of the highest dilution of the sampel required for reducing the numbers of plaques to 50%.

EXPERIMENT 2

Definition of IF inducer:

The active substance of this invention represents and IF inducer because the samples prepared by the methods (a) and (b) are capable of inhibiting the growth of Vesicular stomatitis virus and Vaccinia virus in the lined RK-13 cells of rabbits of the same animal species, but do not inhibit the growth of Vesicular stomatitis virus in L cells of mice i.e. of a different animal species, and morover, their IF activities are inactivated by treating with 0.08% trypsin at 37° C. for 2 hours. It has also been found that the IF induced by the active substance of this invention is stable when dialized against a pH 2 buffer solution at 5° C. for 2 days, unstable on heating at 60° C. for 2 hours, gives no precipitate by centrifugation at 100,000 xg for 2 hours and is non-toxic against the cells at the minimum virus-inhibitory level. The IF induced by the active substance of this invention may be classified into Type-I IF and consists of a complex of α- and β-types. Also it has been observed that IF is induced when the active substance of this invention is used, for example, for treating the cells of bone marrow, lymph node, spleen and the like in vitro or injected into the body of animals, but no IF is induced when applied to treat the primary or continuous cell cultures which are known to induce IF by viral infection or treating with poly I:poly C.

What is claimed is:

1. A process for producing a water-soluble interferon inducer having a moleculer weight of from about 10,000 to about 200,000 from a plant tissue, comprising extracting said interferon inducer with water from the seed of a plant belonging to the genus Carthamus containing said interferon inducer at a temperature of from ambient to the boiling point of the extraction mixture for a period of up to 5 days sufficient to extract the major portion of said interferon inducer present in said tissue, forming a supernatant from the extracted solution, fractionating the supernatant to yield fractions containing the major portion of said interferon inducer present in the supernant, and recovering said interferon inducer therefrom.

2. The process of claim 1 wherein the plant is selected from *Carthamus tinctorius, Carthamus lanatus, Carthamus arborescens, Carthamus baeticus* and variants thereof.

3. The process of claim 1 further comprising the step of extracting oil and fat from the Carthamus seed with an organic solvent capable of mixing with water and incapable of dissolving said interferon inducer prior to extraction with water.

4. The process of claim 1 further comprising the step of a least partly breaking the hull of the seed prior to the extraction with water.

5. The process of claim 1 wherein the extraction is effected with water under alkaline conditions.

6. The process of claim 1 wherein the extraction is effected at a pH of from 7 to 10.

7. The process of claim 1 wherein the extraction is effected with water containing phenol in a concentration of from 20 to 60%.

8. The process of claim 1 wherein the fractionation is effected by ultrafiltration using an ultrafiltration membrane capable of fractionation substances having a molecular weight of from 10,000 to 200,000.

9. A pharmaceutical composition comprising as an active ingredient an interferon inducer made by the process of claim 1 in association with a pharmaceutical carrier or excipient.

10. An amorphous whitish powder effective as an interferon inducer produced by the process of claim 1.

* * * * *